United States Patent
Molaee et al.

(10) Patent No.: US 11,395,913 B2
(45) Date of Patent: Jul. 26, 2022

(54) ECAP RECORDING METHOD AND COCHLEA IMPLANT SYSTEM

(71) Applicant: Oticon Medical A/S, Smørum (DK)

(72) Inventors: Behnam Molaee, Vallauris (FR); Manuel Segovia Martinez, Vallauris (FR)

(73) Assignee: Oticon Medical A/S, Smørum (DK)

( * ) Notice: Subject to any disclaimer, the term of this patent is extended or adjusted under 35 U.S.C. 154(b) by 194 days.

(21) Appl. No.: 16/721,635

(22) Filed: Dec. 19, 2019

(65) Prior Publication Data
US 2021/0187281 A1 Jun. 24, 2021

(51) Int. Cl.
*A61N 1/36* (2006.01)
*A61N 1/05* (2006.01)
*A61N 1/02* (2006.01)

(52) U.S. Cl.
CPC .......... *A61N 1/0541* (2013.01); *A61N 1/025* (2013.01); *A61N 1/36031* (2017.08)

(58) Field of Classification Search
CPC .............. A61N 1/0541; A61N 1/36031; A61N 1/36039; A61N 1/36038
See application file for complete search history.

(56) References Cited

U.S. PATENT DOCUMENTS

| | | | |
|---|---|---|---|
| 8,670,834 B2 * | 3/2014 | Kals | A61N 1/36039 607/57 |
| 2018/0146927 A1 * | 5/2018 | Melman | A61B 5/24 |

* cited by examiner

*Primary Examiner* — George R Evanisko
(74) *Attorney, Agent, or Firm* — Birch, Stewart, Kolasch & Birch, LLP (57) ABSTRACT

A method and a system for measuring a main electrically evoked compound action potential is described. The system may comprise a cochlea implant system which includes an electrode array, and where the electrode array includes at least a stimulator electrode, a first recording electrode and a second recording electrode, and where the first recording electrode is arranged closer to the stimulator electrode than the second recording electrode, a processor electrically in communication with the cochlea implant system. The processor may be configured to apply a stimulation including a first primary stimulation paradigm to the stimulator electrode and to receive a first primary cochlea response signal recorded by the first recording electrode while applying the stimulation, and to receive a first secondary cochlea response signal recorded by the second recording electrode, and determine the main electrically evoked compound action potential based on a difference between the first primary cochlea response signal and the first secondary cochlea response signal.

13 Claims, 10 Drawing Sheets

ECAP RECORDING METHOD AND COCHLEA IMPLANT SYSTEM

FIELD

The present disclosure relates to a method and a cochlea implant system for recording Evoked Compound Action Potential (ECAP).

BACKGROUND

Neural prosthesis, among which cochlea implant systems (CI), are commonly used to replace one or several pathological organs by generating electrical stimulations directly into the nerve fibres to convey a valuable information. A cochlea implant system may comprise a sound processor which is connected to an implant which includes an electrode array, a reference electrode and an inductive interface for communicating with the sound processor. An intrinsic problem to cochlea implant systems, or neural prosthesis in general, is that electrical stimulations need to be calibrated regarding the implanted patient feedback. Such fittings are time consuming and cannot be performed if the patient is unable to inquire the expert to the percept elicited by the stimulation.

Objective measurements (the direct effect of a stimulation into the patient that can be measured by an acquisition device) are the only known possibility to avoid a subjective fitting. In cochlea implant patients, ECAP is an important objective measurement which has several clinical applications. Without a high quality ECAP data these applications may not provide trustable ECAP thresholds, such as T and C levels.

In practice, ECAP is highly contaminated by stimulations artefacts and background noises. The stimulation artefacts may for example be introduced at the stimulation as well as the reference electrodes locations during stimulation. Then, these artefacts appear as nuisance factor for the ECAP, which is acquired after the stimulation.

In order to reduce the artefacts, there are some available ECAP recording paradigms. One may divide these recording paradigms into two main categories: 1) Masking-Based approach, 2) Polarity-Inversion-Based approach. In the first approach, the selective manner activation of neural cells to different parts of a compound stimulation (such as a double-pulse stimulation) is the key concept for artefact removal. In the second approach, inversion of the polarity of the artefact to cathodic and anodic stimulations, and identical activation of neural cells to the stimulations make the principal assumptions for ECAP de-artefacting.

An example of the Polarity-Inversion approach is disclosed by US 2018/0146927A1.

Each of the above mentioned approaches has its own limitations to generate an artefact-free ECAP. In the first approach, there are some linear and/or nonlinearity effects in the system due to electrical interactions between different pulses in a compound stimulation that are not removed from the observed data. An example of the electrical interaction is for example the interaction between the artefact generated by the masker pulse and the artefact generated by the subsequently probe pulse. A further problem is for example that the activation of neural cells is not a perfect pulse selective as we assume. In the second approach, neither activation of neural cells, nor remaining artefact is identical (irrespective of the polarity) in cathodic and anodic stimulations.

SUMMARY

An aspect of the disclosure is to provide a method which provides an improved recording of cochlea response by an electrode array of a cochlea implant system. The cochlea response is determined by an electrically evoked compound action potential (ECAP). The improved recording of the cochlea response involves a reduction in the level of artifacts which may appear in the recorded cochlea response.

According to an aspect, a method for recording cochlea response by an electrode array of a cochlea implant system, wherein the method comprising applying a stimulation including a stimulation paradigm to a stimulator electrode of a plurality of electrodes of the electrode array, and recording a first primary cochlea response signal by a first recording electrode of the plurality of electrodes of the electrode array while applying the stimulation, and recording a first secondary cochlea response signal by a second recording electrode of the plurality of electrodes of the electrode array while applying the stimulation.

The stimulation may be a first stimulation. The recording performed by the recording electrodes may be initiated at about 0.2 ms following stimulus onset. The stimulation may include an anodic part and a cathodic part.

The method is performed when the electrode array is inserted into the cochlea of a recipient.

The first recording electrode may be arranged closer to the stimulator electrode than the second recording electrode. The second recording electrode may be arranged further away from the stimulator electrode than the first recording electrode, such that at least two or more electrodes of the electrode array are arranged between the first recording electrode and the second recording electrode.

A main electrically evoked compound action potential is determined based on a difference between the first primary cochlea response signal and the first secondary cochlea response signal.

The first recording electrode and the second recording electrode may be configured to record simultaneously or sequentially. Based on the stimulation, the first recording electrode records the first primary cochlea response signal which includes a first ECAP signal ($ECAP_1$) and a first artifact ($Art_{11}$), and the second recording electrode records the first secondary cochlea response which includes a second ECAP signal ($ECAP_2$) and a second artifact ($Art_{21}$). The second recording electrode is arranged in such a way that the level of the second ECAP signal is about zero or negligible small. The relation between the first artifact and the second artifact may be determined by a function. The second artifact may be determined by this equation:

$$Art_{21} = f(Art_{11}) = \alpha Art_{11} + Res,$$

wherein $f(\cdot)$ is generally an arbitrary nonlinear time-variant function. It may be estimated $\hat{f}(\cdot)$ based on a priori information about the electrodes (locations, stimulation level, etc.) or upon a numerical method by minimizing a cost function between the recordings of the primary and the secondary electrodes. However, function $f$ may be expressed to a good extent by a zero-order linear function $f = \alpha$. In such a case, $\alpha$ basically expresses the amplitude ratio between $Art_{21}$ and $Art_{11}$. The estimation of a factor is expressed by $\alpha$. Finally, Res is a remained negligible error due to imperfect linear and time-invariant consideration of $f(\cdot)$.

The recorded first primary cochlea response signal ($M_{11}$), may be expressed as follows:

$$M_{11} = ECAP + Art_{11} + Noise_1,$$

and the recorded first secondary cochlea response signal ($M_{21}$), may be expressed as follows:

$$M_{21}=\gamma ECAP+Art_{21}+Noise_2.$$

Noise$_1$ and Noise$_2$ are zero-mean noises, which correspond to stochastic behavior of artefacts and recordings. Without losing generality these terms will be dropped from the equations. The second recording electrode is selected among the plurality of electrodes of the electrodes where it is expected that recorded ECAP is small enough such that $\gamma \simeq 0$, resulting in that the main electrically evoked compound action potential may be determined as follows:

$$M = M_{11} - \frac{1}{\hat{\alpha}}M_{21} = \left(1 - \frac{\gamma}{\hat{\alpha}}\right)ECAP + \left(1 - \frac{\alpha}{\hat{\alpha}}\right)Art_{11} - \frac{Res}{\hat{\alpha}}$$

$$\xrightarrow{Res\cong 0, \gamma \cong 0} M \cong ECAP + \left(1 - \frac{\alpha}{\hat{\alpha}}\right)Art_{11} \xrightarrow{\hat{\alpha}=1} M \cong ECAP + (1-\alpha)Art_{11}$$

The advantage of the method is that the quality of the determined main electrically evoked compound action potential is improved because of the reduced artifacts. The reason for the reduction is mainly because of the arrangement of the recording electrodes in relation to the stimulator electrode. The equation above also shows that if the estimation of function $f$ is discarded and it is substituted simply by $\hat{f}=\hat{\alpha}=1$, still the artefact is reduced by a factor of $\alpha Art_{11}$. In practical cases, α may be very close to unity, especially for common artefact terms appearing on the reference electrode and on primary and secondary recording electrodes.

The stimulation may include a first primary stimulation paradigm and a first secondary stimulation paradigm, and while applying the first primary stimulation paradigm, the first primary cochlea response signal is recorded by the first recording electrode of the electrode array, and while applying the first secondary stimulation paradigm, the first secondary cochlea response signal is recorded by the second recording electrode of the electrode array.

In a cochlea implant system, which does not allow simultaneously recording of cochlea response signal, it is an advantage of applying separate stimulations for the recording electrodes since the quality of the determined main electrically evoked compound action potential is further improved. The reason for the further improved quality is that the time difference from when the stimulation ends and to when the recording ends is reduced for the second recording electrode, and thereby, the remained negligible error due to imperfect linear assumption between the artifacts introduced to the first primary cochlea response signal and the second primary cochlea response signal, respectively, is reduced.

The first primary stimulation paradigm and the first secondary stimulation paradigm may be the same.

The selection of the first recording electrode and/or the second recording electrode is determined based on an ECAP function, and where a cochlea response signal, i.e. a theoretical cochlea response signal, for the first recording electrode and/or the second recording electrode is determined based on the ECAP function. If the determined cochlea response signal is below a first signal threshold level the second recording electrode is selected, and if the cochlea response signal is above the first signal threshold level or a second signal threshold level the first recording electrode is selected.

The first signal threshold level includes a minimum amplitude level of a cochlea response signal, i.e. an ECAP response signal.

The second signal threshold level includes a minimum amplitude level of a cochlea response signal, i.e. an ECAP response signal, and wherein the minimum amplitude level of the second signal threshold level is larger than the minimum amplitude level of the first signal threshold level.

By having the first signal threshold level and/or the second signal threshold level it is possible to select a first and a second recording electrode where the criteria of recording primarily artifacts by the second recording electrode and recording primarily ECAP by the first recording electrode, securing an improved quality of the determined main electrically evoked compound action potential. The second recording electrode may record a negligible ECAP, but the recorded ECAP is so small that it will not interfere and reduce the quality of the determined main electrically evoked compound action potential.

The ECAP function may be determined for each recipient of the electrode array based on a pre-recorded cochlea response signal for each of the plurality of electrodes of the electrode array. This can be accomplished during a fitting session, or continuously, during use of a cochlea implant system including the electrode array. The pre-recorded cochlea response signals and/or the ECAP function may be stored in a memory.

The method may further comprise applying a second stimulation including a second primary stimulation paradigm to the stimulator electrode, and recording a second primary cochlea response signal by the first recording electrode and a second secondary cochlea response signal by the second recording electrode while applying the second stimulation. A main primary cochlea response signal may be determined based on a difference between the first primary cochlea response signal and the second primary cochlea response signal. A main secondary cochlea response signal may be determined based on a difference between the first secondary cochlea response signal and the second secondary cochlea response signal, and the main electrically evoked compound action potential may be determined based on a difference between the main primary cochlea response signal and the main secondary cochlea response signal.

The method may further comprise applying multiple stimulations, where each of the multiple stimulations includes a stimulation paradigm.

While applying the first stimulation, which includes a first primary stimulation paradigm which has a single stimulation pulse, the first recording electrode records a first primary cochlea response signal which includes ECAP and artifacts, $Art_{11}$. The first primary cochlea response signal may be expressed as:

$$M_{11}=ECAP+Art_{11}.$$

The second stimulation includes a second primary stimulation paradigm which has a masker stimulation pulse and a probe stimulation pulse, and the masker stimulation pulse is used to set the auditory nerve of the cochlea in a refractory state, and the probe stimulation pulse is transmitted to the stimulation electrode after the masker stimulation pulse. In a different example, the masker stimulation pulse (or any preconditioning stimulation paradigm) may be transmitted to a first stimulation electrode of the electrode array, and the probe stimulation pulse may be transmitted to a second stimulation electrode, wherein the masker stimulation pulse is applied as a stimulation to the recipient before the probe stimulation pulse is applied. The first recording electrode records a second primary cochlea response signal while applying the second stimulation, and more specifically, when the probe stimulation pulse is applied. The second primary cochlea response signal includes only artifacts, $Art_{12}$, recorded by the first recording electrode. The second primary cochlea response may be expressed as:

$$M_{12} = Art_{12}$$

The main primary cochlea response signal ($M_1$) may be determined based on a difference between the first primary cochlea response (Mu) signal and the second primary cochlea response signal ($M_{12}$). The main primary cochlea response signal may be expressed as:

$$M_1 = M_{11} - M_{12} = ECAP + Art_1,$$

where $Art_1$ represents the overall artefact over the primary recording electrode, and is equal to $Art_{11} - Art_{12}$.

Thereby, the measured artifact recorded in the first recording electrode is reduced significantly as $Art_1 \ll Art_{11}$.

While applying the first stimulation, which includes a first secondary stimulation paradigm which has a single stimulation pulse, the second recording electrode records a first secondary cochlea response signal which includes γECAP and artifacts, $Art_{21}$. The first secondary cochlea response signal may be expressed as:

$$M_{21} = \gamma ECAP + Art_{21},$$

γECAP is very small because the second electrode is positioned further away from the stimulator electrode than the first recording electrode (γ≈0). The artifact $Art_{21}$ may be determined by a function, e.g. a linear function, in relation to the artifact, $Art_{11}$ (i.e., $Art_{21} = f(Art_{11})$):

$$M_{21} = \gamma ECAP + f(Art_{11}).$$

The second stimulation includes a second secondary stimulation paradigm which has a masker stimulation pulse and a probe stimulation pulse. The second recording electrode records a second secondary cochlea response signal while applying the second stimulation, and more specifically, when the probe stimulation pulse is applied. The second secondary cochlea response signal includes only artifacts, $Art_{22}$, recorded by the second recording electrode. The second secondary cochlea response may be expressed as:

$$M_{22} = Art_{22}.$$

The artifact $Art_{22}$ may be determined by a function, e.g. a linear function, in relation to the artifact, $Art_{12}$ (i.e., $Art_{22} = f(Art_{12})$):

$$M_{22} = f(Art_{12}).$$

The main secondary cochlea response signal ($M_2$) may be determined based on a difference between the first secondary cochlea response ($M_{21}$) signal and the second secondary cochlea response signal ($M_{22}$). The main secondary cochlea response signal may be expressed as:

$$M_2 = M_{21} - M_{22} = \gamma ECAP + f(Art_{11}) - f(Art_{12}) \approx f(Art_{11} - Art_{12}) \therefore M_2 \approx f(Art_1) = Art_2$$

where $Art_2$ represents the overall artefact over the secondary recording electrode. $f(Art_1)$ can be expressed to a good extent by a zero-order linear function, and the main secondary cochlea response signal may be expressed as:

$$M_2 = \alpha Art_1 + Res,$$

where α is a linear function between artifacts $Art_2$ and $Art_1$ recorded by the second electrode and artifacts recorded by the first electrode, respectively. Res is a remained negligible error due to imperfect linear assumption.

The main electrically evoked compound action potential may be determined based on a difference between the main primary cochlea response signal and the main secondary cochlea response signal. The main electrically evoked compound action potential may be expressed as:

$$M = M_1 - \frac{1}{\hat{\alpha}} M_2 = \left(1 - \frac{\gamma}{\hat{\alpha}}\right) ECAP + \left(1 - \frac{\alpha}{\hat{\alpha}}\right) Art_1 - \frac{Res}{\hat{\alpha}}$$

$$\xrightarrow{Res \cong 0, \gamma \cong 0} M \cong ECAP + \left(1 - \frac{\alpha}{\hat{\alpha}}\right) Art_1 \xrightarrow{\hat{\alpha}=1} M \cong ECAP + (1 - \alpha) Art_1$$

In this method the measured artifact recorded in the first recording electrode ($Art_1$) is already reduced significantly when only utilizing the first recording electrode, as $Art_1 \ll Art_{11}$. In addition, when using both the first recording electrode and the second recording electrode, the final remaining artifact may be even more reduced as the factor α is used to compensate the difference between two already significantly reduced artefacts $Art_1$ and $Art_2$.

As in the previous case, estimation of a can be considered as an optional step. However, a may be determined using minimizing a cost function between recordings of the primary and the secondary electrodes. α may also be estimated a priori via a linear function between recorded artifacts of two or more electrodes of the electrode array, and/or via the ECAP function. The linear function and/or the ECAP function may be stored in a memory unit of a system being a fitting system connected to a cochlea implant system, or of a system being a cochlea implant system where a processor is part of the cochlea implant system.

The first primary cochlea response signal and the first secondary cochlea response signal are recorded based on a single stimulation pulse, and the second primary cochlea response signal and the second secondary cochlea response signal are recorded based on multiple stimulation pulses, wherein the multiple stimulation pulses include at least a masker stimulation pulse and a probe stimulation pulse. The masker stimulation pulse is transmitted to the electrode array after the probe stimulation pulse.

For the multiple stimulation pulses (relating to the second primary cochlea response signal and the second secondary cochlea response signal), the stimulating electrode of the masker pulses and the stimulating electrode of the probe pulse may or may not be identical. In such a case, 'S' refers to the stimulating electrode of the probe pulse, and 'S_aux' (auxiliary stimulating electrode) refers to the stimulating electrode which is used for the masker pulses.

The applying of the stimulation is provided at a first time, and the applying of the second stimulation is provided at a second time, and wherein a time difference between the first time and the second time is below 20 ms, 10 ms, 1 ms or 0.5 ms.

According to a further aspect, a system is provided for measuring a main electrically evoked compound action potential. The system comprising a cochlea implant system which includes an electrode array, and where the electrode array includes at least a stimulator electrode, a first recording electrode and a second recording electrode, and where the first recording electrode is arranged closer to the stimulator electrode than the second recording electrode. The cochlea implant system or the system may include a processor which is electrically in communication with the cochlea implant system. The processor is configured to apply a stimulation including a first primary stimulation paradigm to the stimulator electrode and to receive a first primary cochlea response signal recorded by the first recording electrode while applying the stimulation, and to receive a first secondary cochlea response signal recorded by the second recording electrode, and to determine the main electrically evoked compound action potential based on a difference between the first primary cochlea response signal and the first secondary cochlea response signal.

The system may include a fitting system, e.g. a computer handled by a hearing caring professional, which is electrically connected to the cochlea implant system. The cochlea implant system includes at least an external part inductively connected with an implantable part which is electrically connected to the electrode array. The cochlea implant system may only include an implantable part which is electrically connected to the electrode array. The processor may be part of the external part, the implantable part or the fitting system.

The external part and/or the implantable part may comprise at least a microphone configured to received and convert an acoustical input to an audio input signal, a sound processor configured to receive the audio input signal and process the audio input signal into pulse encoded signals. The sound processor is then configured to transmit the pulse encoded signals to the electrode array, where one or more of electrodes of the electrode array are configured to provide electrically stimulations directly to the nerve fibers of the cochlea. The memory unit defined early, may be part of the fitting system, the external part and/or the implantable part.

The stimulation includes a first secondary stimulation paradigm, and while applying the first secondary stimulation paradigm the first secondary cochlea response signal is recorded by the second recording electrode of the electrode array.

The processor is further configured to apply another stimulation including a second primary stimulation paradigm to the stimulator electrode, and to receive a second primary cochlea response signal recorded by the first recording electrode while applying the another stimulation, and to receive a second secondary cochlea response signal recorded by the second recording electrode while applying the another stimulation. The processor is further configured to determine a main primary cochlea response signal based on the first primary cochlea response signal and the second primary cochlea response signal, and to determine a main secondary cochlea response signal based on the first secondary cochlea response signal and the second secondary cochlea response signal. The processor is further configured to determine the main electrically evoked compound action potential based on a difference between the main primary cochlea response signal and the main secondary cochlea response signal.

The second stimulation may include a second secondary stimulation paradigm, and while applying the second secondary stimulation paradigm the second secondary cochlea response signal is recorded by the second recording electrode of the electrode array.

The first primary cochlea response signal and the first secondary cochlea response signal include a single stimulation pulse, and the second primary cochlea response signal and the second secondary cochlea response signal include multiple stimulation pulses, wherein the multiple stimulation pulses include at least a masker stimulation pulse and at least a probe stimulation pulse.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, etc. (collectively referred to as "elements"). Depending upon particular application, design constraints or other reasons, these elements may be implemented using other equivalent elements.

A hearing aid is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. Such audible signals may be provided in the form of an acoustic signal transferred as mechanical vibrations to the user's inner ears through bone structure of the user's head.

A "system" refers to a system comprising one or two hearing aids, and a "binaural hearing system" refers to a system comprising two hearing aids where the devices are adapted to cooperatively provide audible signals to both of the user's ears or the hearing aid of bone conduction type may be part of a bimodal system comprising a cochlea implant and a bone conduction hearing aid. The system may further include auxiliary device(s) that communicates with at least one hearing aid, the auxiliary device affecting the operation of the hearing aids and/or benefitting from the functioning of the hearing aids. A wired or wireless communication link between the at least one hearing aid and the auxiliary device is established that allows for exchanging information (e.g. control and status signals, possibly audio signals) between the at least one hearing aid and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing aid. The remote control is adapted to control functionality and operation of the at least one hearing aids. The function of the remote control may be implemented in a SmartPhone or other electronic device, the SmartPhone/electronic device possibly running an application that controls functionality of the at least one hearing aid.

In general, a hearing aid includes i) an input unit such as a microphone for receiving an acoustic signal from a user's surroundings and providing a corresponding input audio signal, and/or ii) a receiving unit for electronically receiving an input audio signal. The hearing aid further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer for providing mechanical vibrations either transcutaneously or percutaneously to the skull bone.

Figure 1:
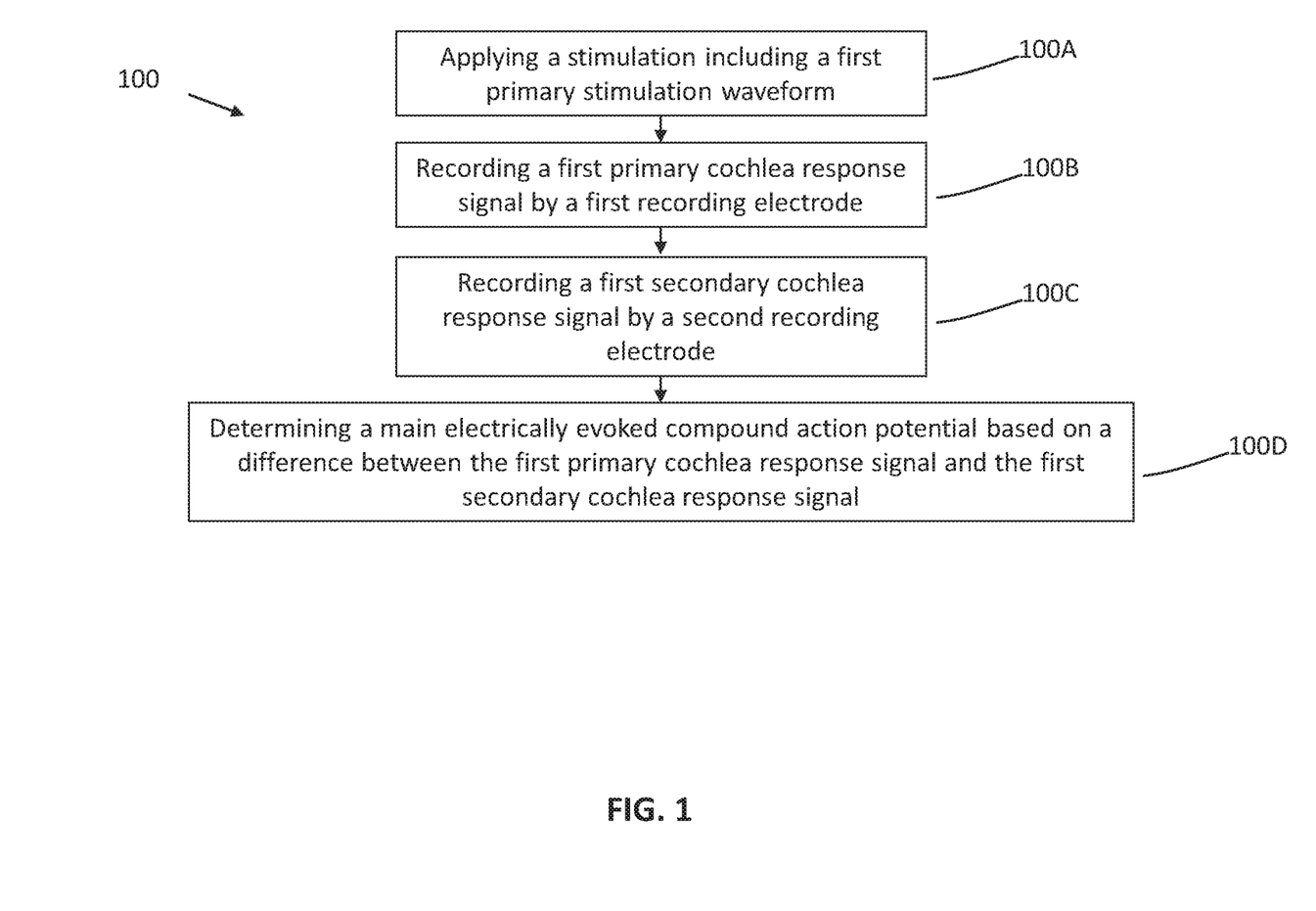
FIG. 1 illustrates a flow diagram of a method.

FIG. 1 illustrates a flow diagram of the method (100) for recording cochlea response by an electrode array of a cochlea implant system, wherein the method comprising applying (100A) a stimulation including a stimulation paradigm to a stimulator electrode of a plurality of electrodes of the electrode array, recording (100B) a first primary cochlea response signal by a first recording electrode of the plurality of electrodes of the electrode array while applying the stimulation, recording (100C) a first secondary cochlea response signal by a second recording electrode of the plurality of electrodes of the electrode array while applying the stimulation, and the second recording electrode is arranged further away from the stimulator electrode than the first recording electrode, such that two or more electrodes of the electrode array are arranged between the first recording electrode and the second recording electrode. Furthermore, the method comprises determining (100D) a main electrically evoked compound action potential based on a difference between the first primary cochlea response signal and the first secondary cochlea response signal.

Figure 2A:
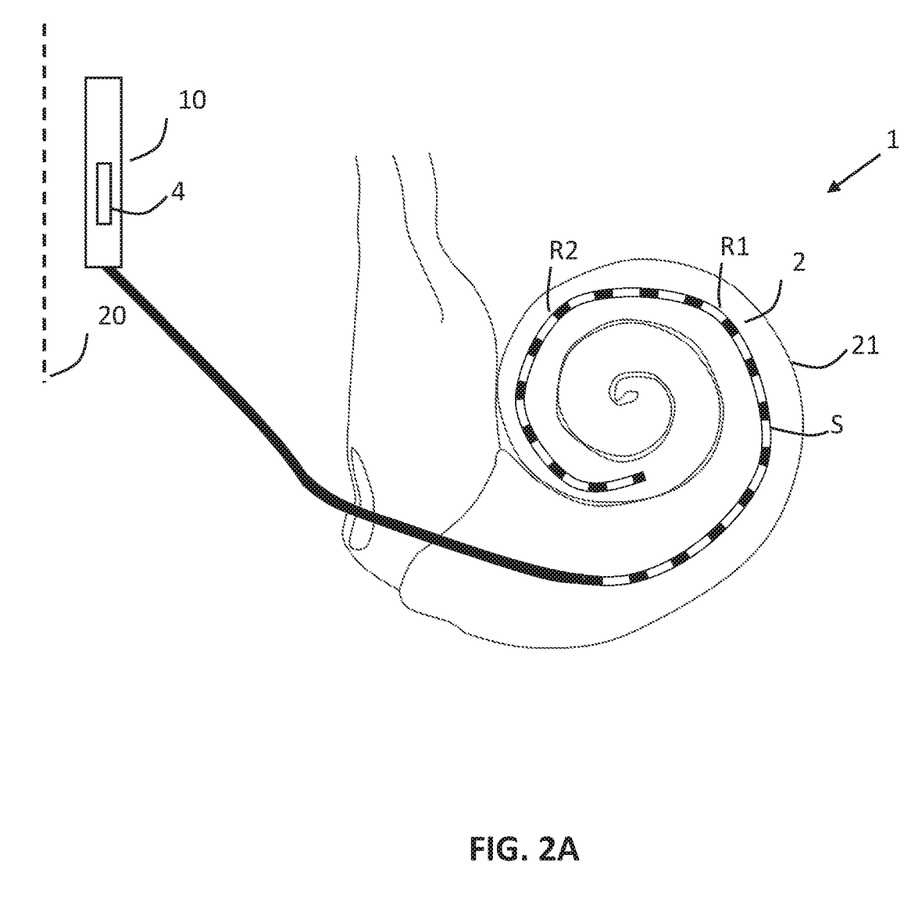
FIGS. 2A to 2C illustrate examples of a system.
Figure 2B:
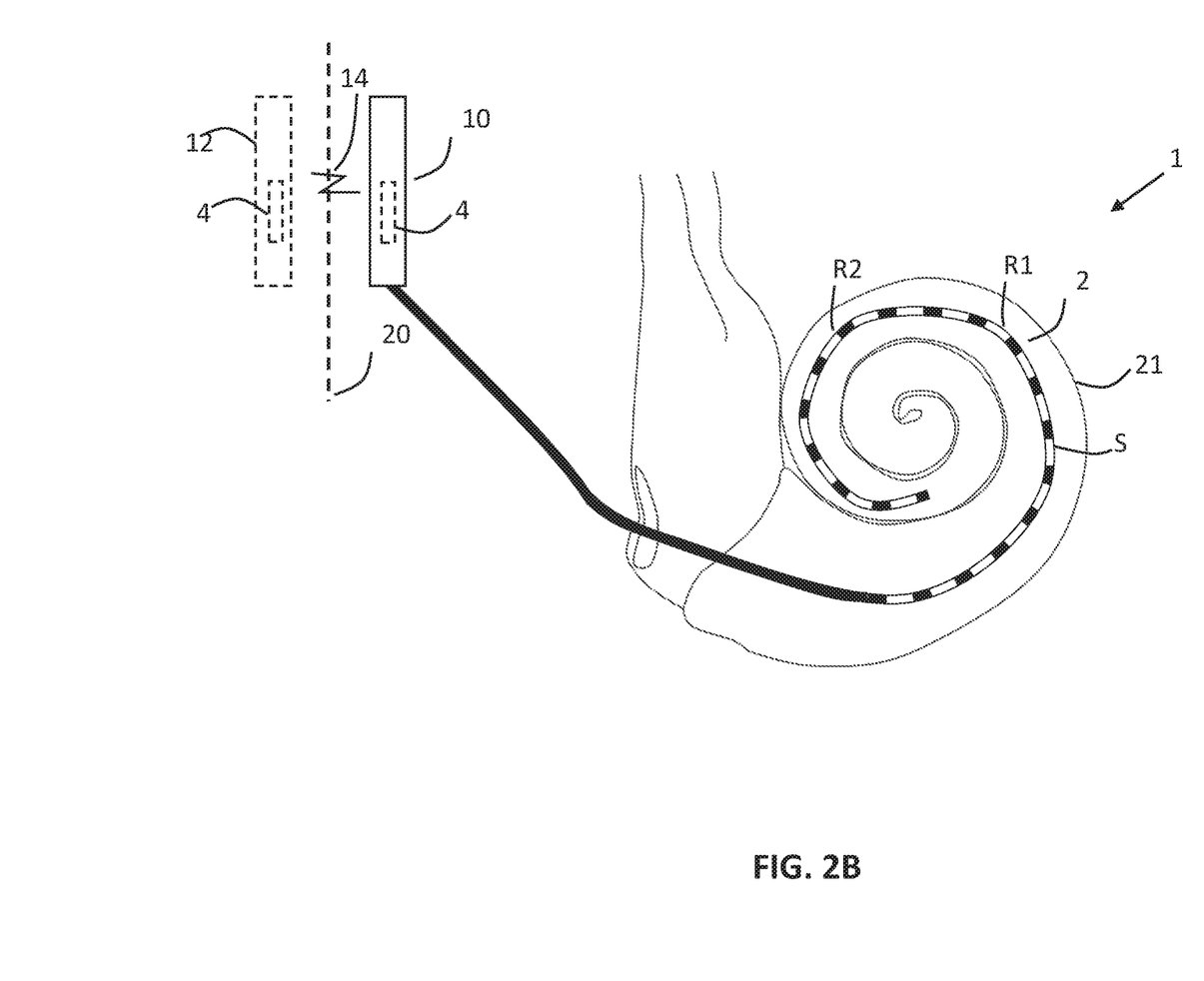
Figure 2C:
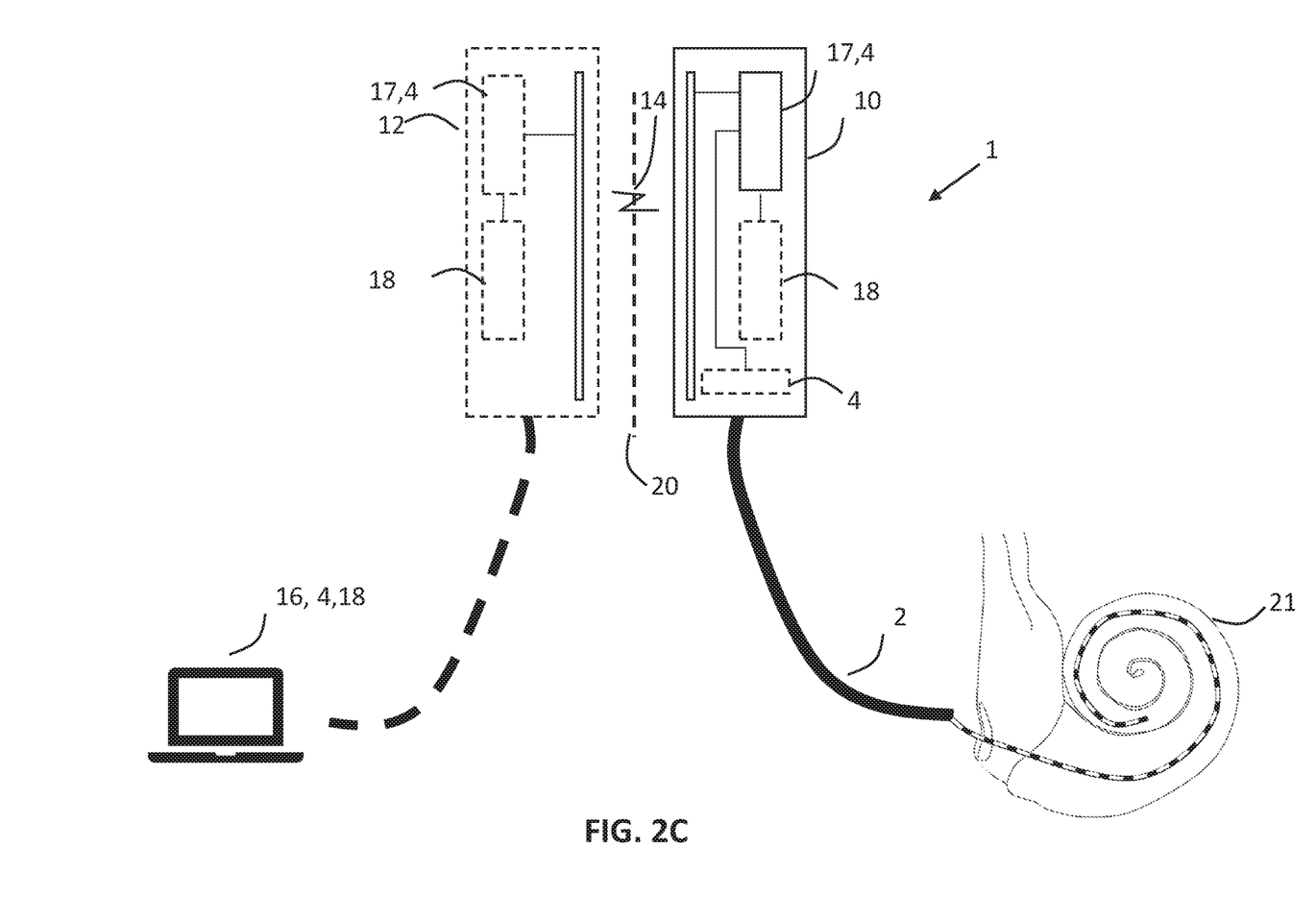

FIGS. 2A to 2C illustrate examples of the system 1 for measuring the main electrically evoked compound action potential, where an electrode array is implanted into a cochlea 21 of a recipient. The cochlea implant system (10, 12) which includes an electrode array 2, and where the electrode array 2 includes at least a stimulator electrode S, a first recording electrode R1 and a second recording electrode R2, and where the first recording electrode R1 is arranged closer to the stimulator electrode S than the second recording electrode R2. The system 1 further includes a processor 4 electrically in communication with the cochlea implant system (10, 12), and the processor 4 is configured to apply a stimulation including a first primary stimulation paradigm to the stimulator electrode S and to receive a first primary cochlea response signal $M_{11}$ recorded by the first recording electrode R1 while applying the stimulation, and to receive a first secondary cochlea response signal $M_{21}$ recorded by the second recording electrode R2. The processor 4 is further configured to determine the main electrically evoked compound action potential M based on a difference between the first primary cochlea response signal $M_{11}$ and the first secondary cochlea response signal $M_{21}$. In another example, the processor is further configured to apply another stimulation including a second primary stimulation paradigm to the stimulator electrode, and to receive a second primary cochlea response signal $M_{12}$ recorded by the first recording electrode while applying the another stimulation, and to receive a second secondary cochlea response signal $M_{22}$ recorded by the second recording electrode while applying the another stimulation. The processor 4 is further configured to determine a main primary cochlea response signal $M_1$ based on the first primary cochlea response signal Mu' and the second primary cochlea response signal $M_{12}$, and to determine a main secondary cochlea response signal $M_2$ based on the first secondary cochlea response signal $M_{21}$ and the second secondary cochlea response signal $M_{22}$. The processor 4 is configured to determine the main electrically evoked compound action potential M based on a difference between the main primary cochlea response signal $M_1$ and the main secondary cochlea response signal $M_2$.

FIG. 2A, illustrates the system 1 which includes the cochlea implant system, and in this specific example, the cochlea implant system includes an implantable part 10 implanted under a skin 20 of the recipient of the electrode array 2. The electrode array 12 is connected to the implantable part 10. In a further example, and not shown in FIG. 2A, the implantable part may include a sound processor, at least a microphone, and/or a memory unit.

FIG. 2B illustrates the system 1 which in this specific example includes an external part 12 and the implantable part 10, where the implantable part 10 is connected to the electrode array 2. In this example, the external part 12 and the implantable part 10 are inductively 14 connected. In this example the processor 4 may be part of the external 12 or the implantable part 10.

FIG. 2C illustrates the system 1 which in this specific example includes a fitting system 16 which is connected to the external part 12 either directly or indirectly via a hearing aid wired connected to the external part 12. The hearing aid is not shown in FIG. 2C. The hearing aid may be a behind-the-ear hearing aid. The processor 4 may be within the fitting system 16, the external part 12 or the implantable part 10. In this specific example the processor 4 may be part of a sound processor 17 or a separate unit as illustrated within the implantable part 10. The system 1 includes a memory unit 19, which may be within the fitting system 16, the external part 12 and/or the implantable part.

Figure 3A:
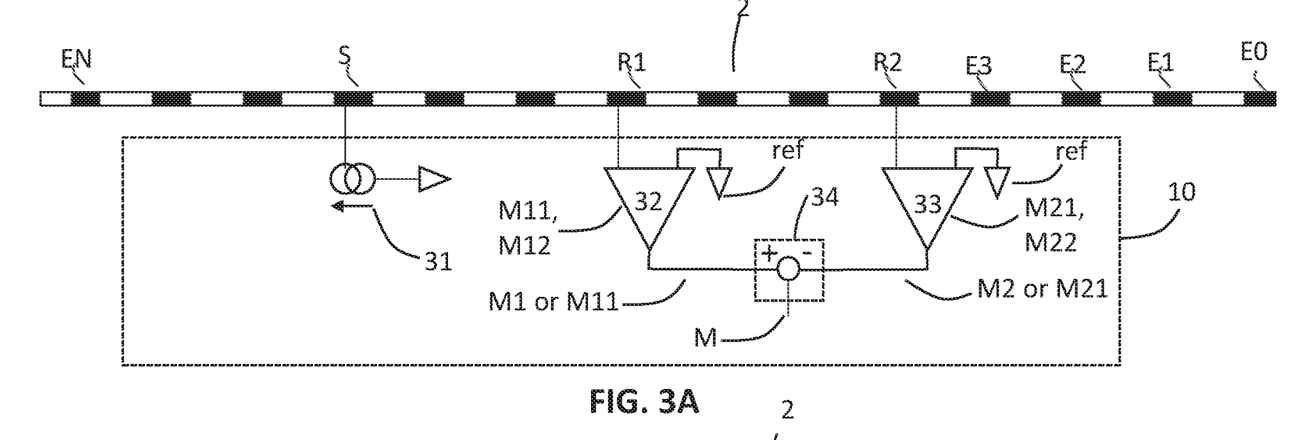
FIGS. 3A and 3B illustrate an electrode array being connected to an implantable part.
Figure 3B:
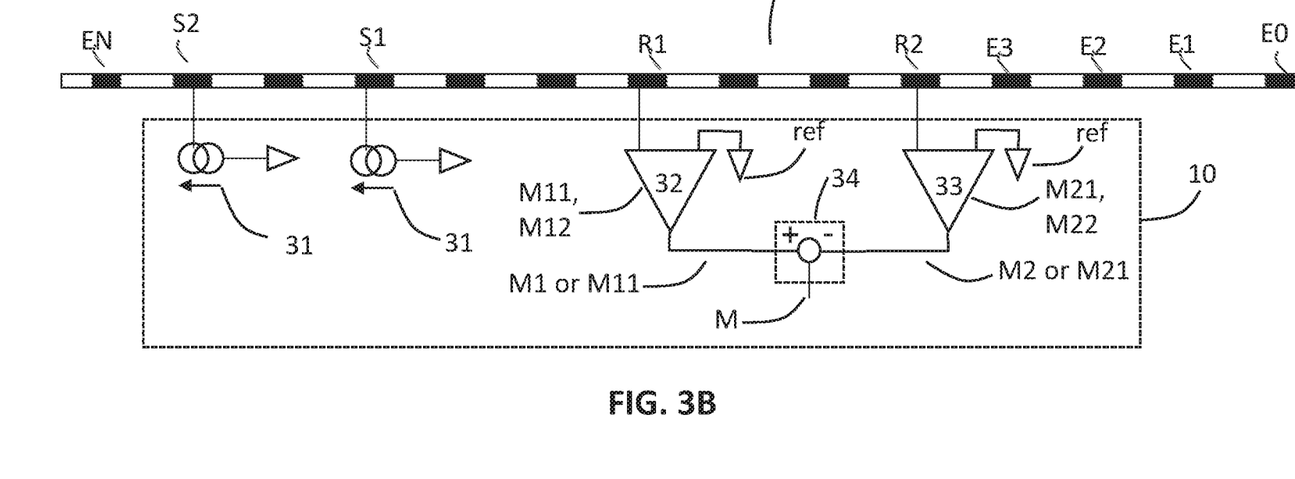

FIGS. 3A and 3B illustrate the electrode array 2 being connected to the implantable part 10. FIG. 3A illustrates that the implantable part includes a stimulation generator 31 which is connected to the stimulator electrode S. In another example, the stimulation generator 31 may be within the external part 12. In this specific example, the first recording electrode is connected to a comparator 32, wherein the comparator 32 is configured to receive the first primary cochlea response signal Mu', and in another example, also the second primary cochlea response signal $M_{12}$. In one example, the comparator 32 is configured to forward the first primary cochlea response signal $M_{11}$ to a subtractor 34, and in another example, the comparator 32 is configured to transmit a main primary cochlea response signal $M_1$ to the subtractor 34. Furthermore, in this specific example, the second recording electrode is connected to a comparator 33, wherein the comparator 33 is configured to receive the first secondary cochlea response signal $M_{21}$, and in another example, also the second secondary cochlea response signal $M_{22}$. In one example, the comparator 33 is configured to forward the first secondary cochlea response signal $M_{21}$ to a subtractor 34, and in another example, the comparator 33 is configured to transmit a main secondary cochlea response signal $M_2$ to the subtractor 34.

The subtractor 34 may be implemented into the implantable part 10 as a hardware subtractor or a software based subtractor. The software based subtractor may be implemented into the processor 4.

The subtractor 34 is configured to determine the main electrically evoked compound action potential M based on the first primary cochlea response signal $M_{11}$ and the first secondary cochlea response signal $M_{21}$ or based on the main primary cochlea response signal $M_1$ and the main secondary cochlea response signal $M_2$.

FIG. 3B illustrates a similar configuration of the electrode array 2 and the implantable part 10, wherein a first stimulation electrode (S1) and a second stimulation electrode (S2) are connected to a stimulation generator 31. In an example where applying a second stimulation which includes a second primary stimulation paradigm and/or a second secondary stimulation paradigm, wherein both paradigms include a masker stimulation pulse (or any preconditioning stimulation paradigm) and a probe stimulation pulse. The first stimulation electrode (S1) is configured to received either the masker stimulation pulse or the probe stimulation pulse, and the second stimulation electrode (S2) is configured to received either the masker stimulation pulse or the probe stimulation pulse.

Figure 4A:
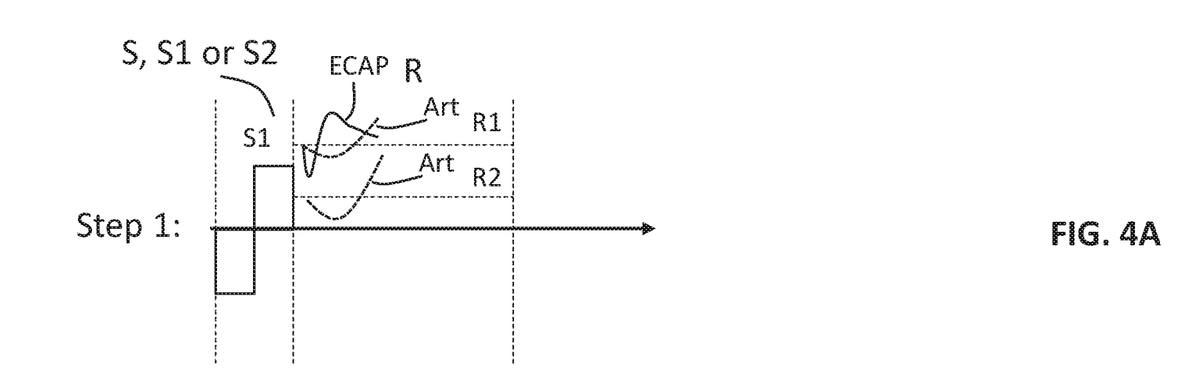
FIGS. 4A to 4D illustrate examples of stimulation and recording schemes provided by the method 100 and the system 1.

FIG. 4A to 4D, illustrate examples of the stimulation and recording schemes provided by the method 100 and the system 1. FIG. 4A illustrates the stimulation S1 provide by the stimulation electrode (S, S1 or S2), and which in this specific, the stimulation S1 is a biphasic pulse. After the end of the stimulation S1, the first and the second recording electrode (R1, R2) initiates the recording of the cochlea response signals ($M_{11}$, $M_{21}$), simultaneously. The first recording electrode R1 records both an ECAP and artifacts Art, and the second recording electrode R2 records mainly artifacts Art.

Figure 4B:
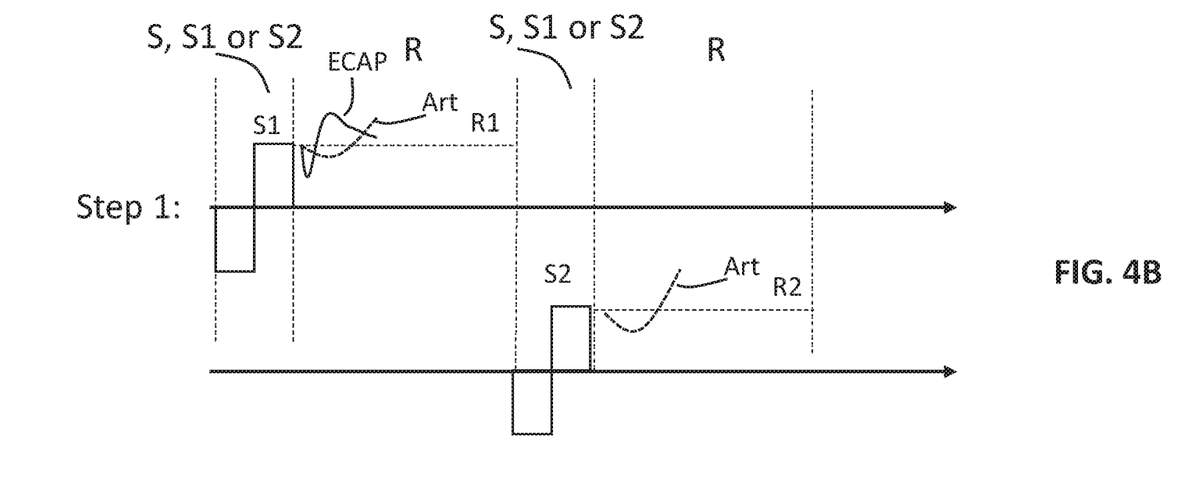

FIG. 4B illustrates a stimulation S1 provided by the stimulation electrode (S, S1 or S2), and where the first recording electrode R1 initiates the recording of the first primary cochlea response signal $M_{11}$ after the end of the stimulation period. After the stimulation S1, a second stimulation S2 is provided by the stimulation electrode S, and the second recording electrode R2 initiates the recording of the first secondary cochlea response signal $M_{21}$ after the end of the stimulation period S2.

Figure 4C:
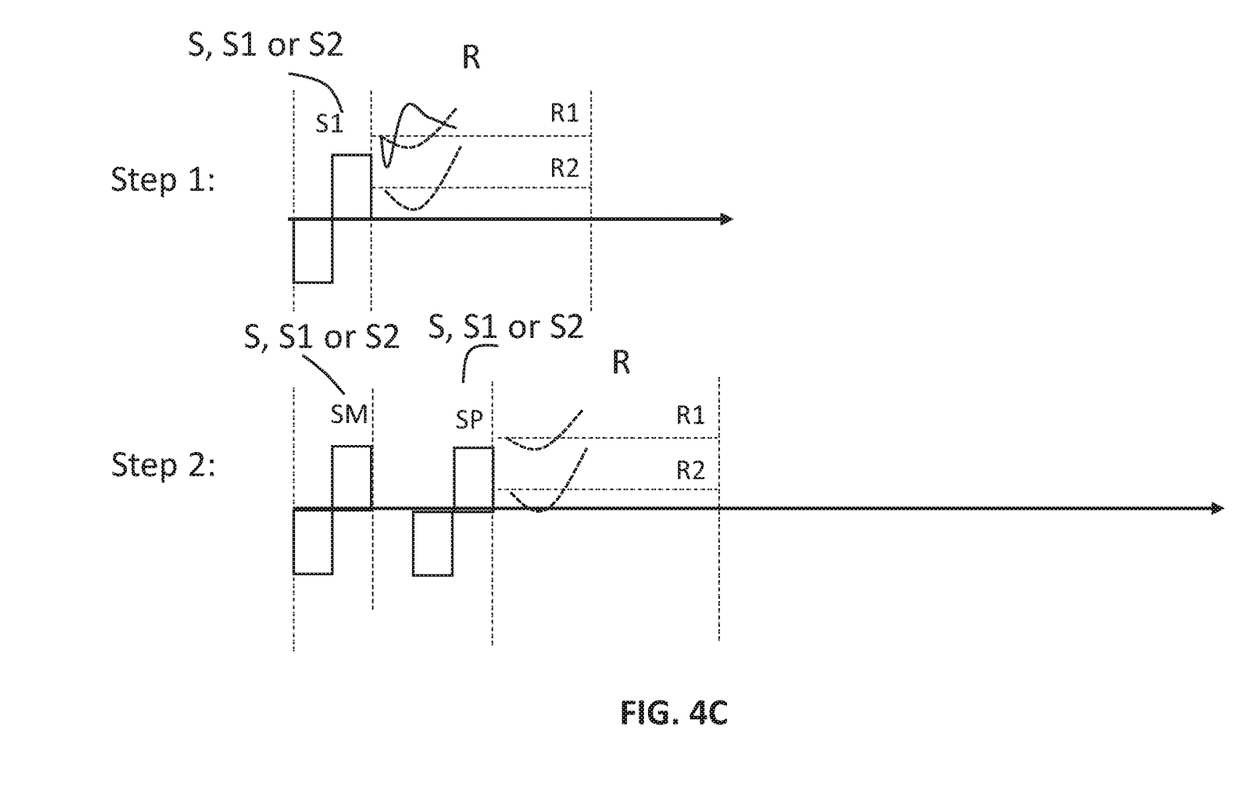

FIG. 4C illustrates a specific example where both a first stimulation and a second stimulation is provided by the stimulation electrode (S, S1 or S2), and where the first stimulation includes a single pulse S1, e.g. a single biphasic pulse, and the second stimulation includes multiple biphasic stimulation pulses (SM, SP). The multiple stimulation pulses include a masker stimulation pulse SM (or any preconditioning stimulation paradigm) and a probe stimulation pulse SP. In this specific example, the stimulation electrode (S, S1 or S2) provides the first stimulation, and both recording electrodes (R1, R2) initiate the recording of the first primary cochlea response signal Mu and the first secondary cochlea response signal $M_{21}$, respectively and simultaneously, after the end of the stimulation period S1. Furthermore, the stimulation electrode (S, S1 or S2) provides the second stimulation (SM, SP), and first, the masker stimulation pulse SM is provided by the stimulation electrode (S, S1 or S2), and after the masker stimulation pulse SM, the stimulation electrode (S, S1 or S2) provides the probe stimulation pulse SP, and both recording electrodes (R1, R2) initiates the recording of the second primary cochlea response signal $M_{21}$ and the second secondary cochlea response signal $M_{22}$, respectively and simultaneously, after the end of the probe stimulation pulse period SP.

Figure 4D:
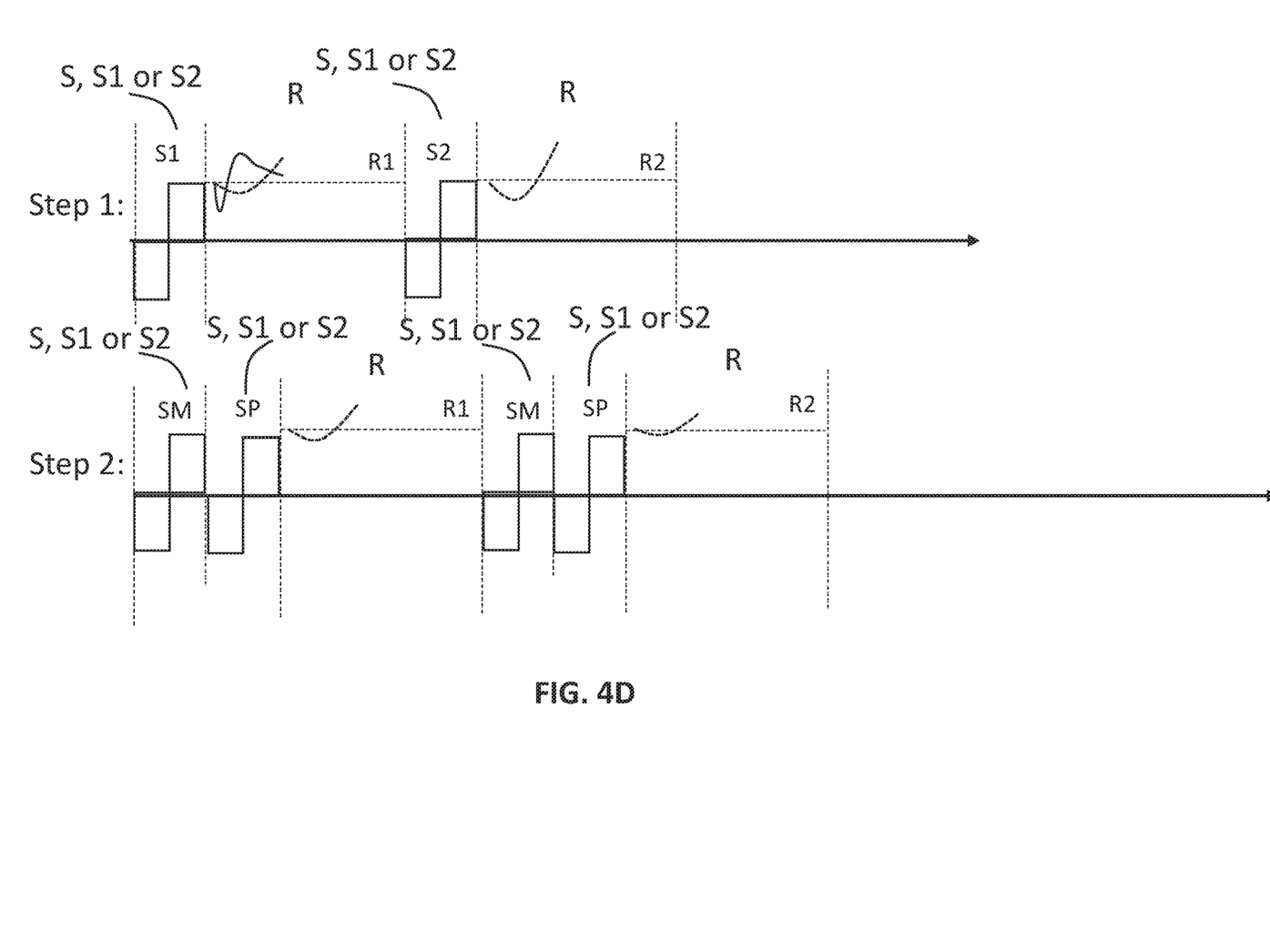

FIG. 4D illustrates a specific example where both a first stimulation and a second stimulation is provided by the stimulation electrode (S, S1 or S2), and where the first stimulation includes a single pulse S1, e.g. a single biphasic pulse, and the second stimulation includes multiple biphasic stimulation pulses (SM, SP). The multiple stimulation pulses include a masker stimulation pulse SM (or any preconditioning stimulation paradigm) and a probe stimulation pulse SP. In this specific example, the stimulation electrode S provides the first stimulation, and the first recording electrode R1 initiates the recording of the first primary cochlea response signal Mu after the end of the stimulation period S1. After the first stimulation S1, the stimulation electrode S, the first stimulation electrode or the second stimulation electrode S2 provides the second stimulation S2, and the second recording electrode R2 initiates the recording of the first secondary cochlea response signal $M_{21}$ after the end of the stimulation period S2. Furthermore, the stimulation electrode S, the first stimulation electrode and/or the second stimulation electrode S2, provides the second stimulation (SM, SP), and first, the masker stimulation pulse SM is provided by the stimulation electrode S or by the first stimulation electrode, and after the masker stimulation pulse SM is applied as a stimulation to the recipient, the stimulation electrode S or the second stimulation electrode provides the probe stimulation pulse SP. The first recording electrode initiates the recording of the second primary cochlea response signal $M_{12}$ after the end of the probe stimulation pulse period SP. Furthermore, the stimulation electrode S, the first stimulation electrode S1 or the second stimulation electrode S2 provides yet again masker stimulation pulse SM and probe stimulation pulse SP, and the second recording electrode initiates the recording of the second secondary cochlea response signal $M_{22}$ after the end of the probe stimulation pulse period SP.

In another example, the recordings performed by the recording electrodes may be initiated at about 0.2 to 1 ms following stimulus onset (S1, S2, SP).

A time delay may be provided or applied between the masker stimulation pulse (SM) and the probe stimulation pulse (SP). The time delay is not illustrated in FIGS. 4A to 4D.

Figure 5A:
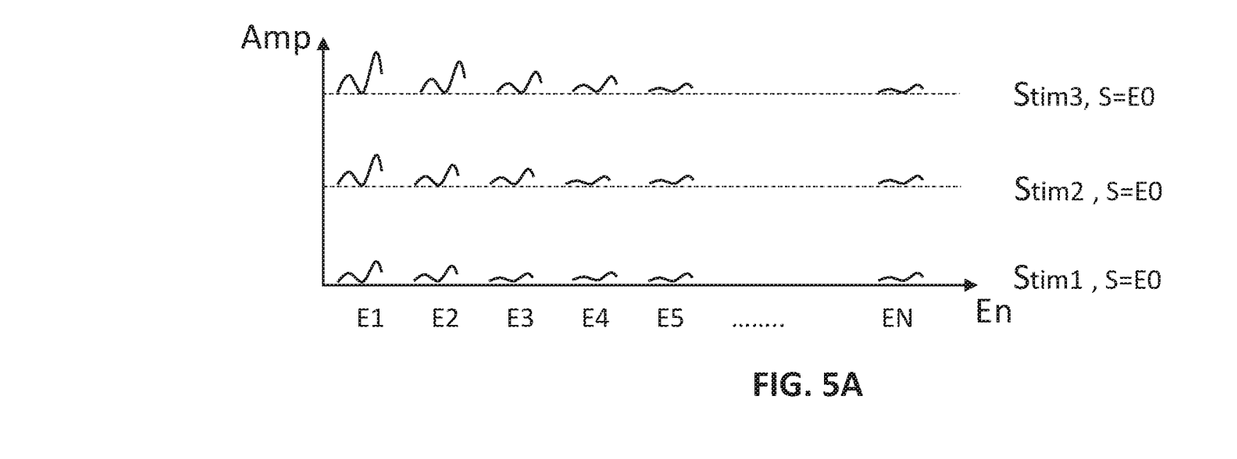
FIGS. 5A and 5B illustrate examples on recordings which may be stored in a memory unit.
Figure 5B:
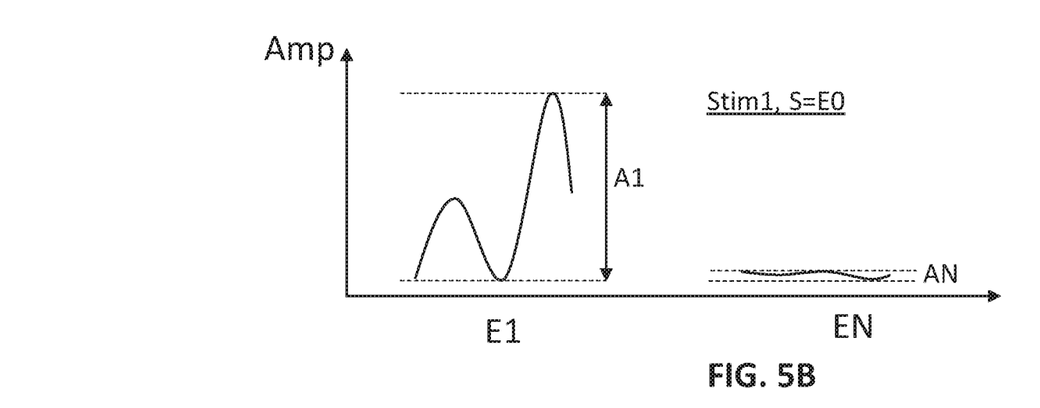

FIGS. 5A and 5B, illustrate examples on recordings which may be stored in a memory unit 18. FIG. 5A includes cochlea response signal recorded for each electrodes E1-EN, at one or more different stimulation levels (Stim1, Stim2, Stim3) and for the same stimulation electrode S, which in this specific example is electrode number 0, (E0). The recorded cochlea response signals include at least a measure of an amplitude A1 of the cochlea response signal, see FIG. 5B, and the amplitude for each of the electrodes decreases when moving further away from the stimulation electrode E0.

Figure 6:
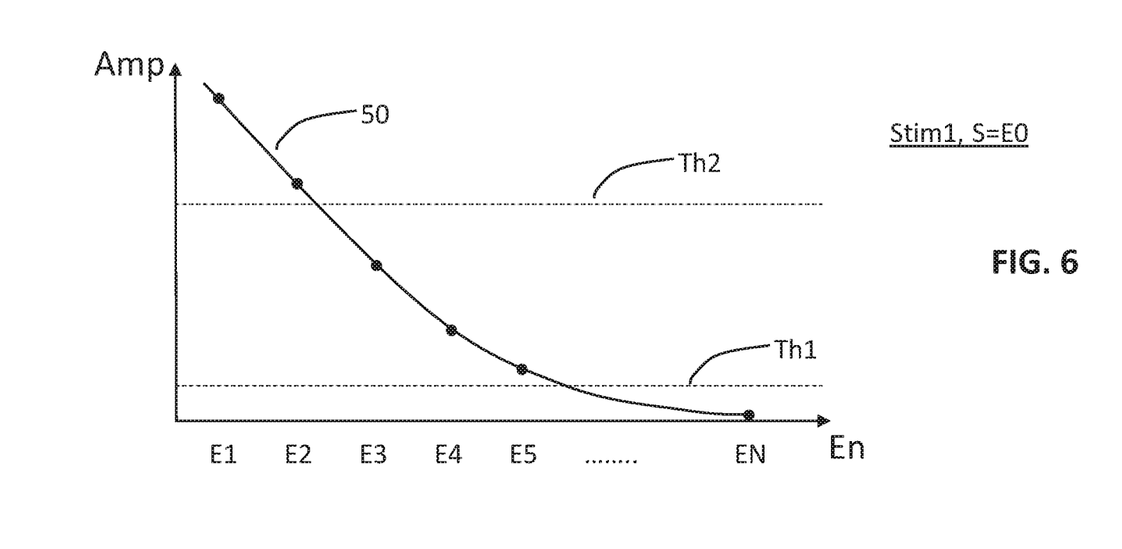
FIG. 6 illustrates an example of an ECAP function.

FIG. 6 illustrates an example of an ECAP function 50, a first signal threshold level TH1 and a second signal threshold level TH2. The ECAP function includes the measured amplitudes of the recorded cochlea response signal of each electrode at a specific stimulation level (Stim1) provided by the stimulation electrode, S. Among a group of electrodes which has an amplitude A above the second signal threshold level TH2, may be selected as the first recording electrode R1, and among a group of electrodes which has an amplitude below the first signal threshold level TH1 may be selected as the second recording electrode R2.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, elements, components, and/or steps but do not preclude the presence or addition of one or more other features, elements, components, and/or steps thereof. It will also be understood that when an element is referred to as being "connected" or "coupled" to another element, it can be directly connected or coupled to the other element, but an intervening element may also be present, unless expressly stated otherwise. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The scope should be judged in terms of the claims that follow.

The invention claimed is:

1. A method for recording cochlea response by an electrode array of a cochlea implant system, wherein the method comprising;
   applying stimulations corresponding to a first primary stimulation paradigm and a first secondary stimulation paradigm, respectively, to a stimulator electrode of a plurality of electrodes of the electrode array,
   recording a first primary cochlea response signal by a first recording electrode of the plurality of electrodes of the electrode array while applying the stimulation corresponding to the first primary stimulation paradigm,
   recording a first secondary cochlea response signal by a second recording electrode of the plurality of electrodes of the electrode array while applying the stimulation corresponding to the first secondary stimulation paradigm, the second recording electrode being arranged further away from the stimulator electrode than the first recording electrode, such that two or more electrodes of the electrode array are arranged between the first recording electrode and the second recording electrode,
   calculating a difference between the first primary cochlea response signal and the first secondary cochlea response signal, and using the calculated difference to determine a main electrically evoked compound action potential,
wherein the method further comprises using an ECAP function to select the first recording electrode and/or the second recording electrode, and wherein a pre-recorded cochlea response signal for each of the plurality of electrodes of the electrode array is used to determine the ECAP function.

2. A method according to claim 1, wherein a memory stores the pre-recorded cochlea response signals and/or the ECAP function.

3. A method according to claim 2, wherein the method further comprises using the ECAP function to select the second recording electrode and to determine a cochlea response signal for the second recording electrode, which is below a first signal threshold level.

4. A method according to claim 1, wherein the method further comprises using the ECAP function to select the second recording electrode and to determine a cochlea response signal for the second recording electrode, which is below a first signal threshold level.

5. A method according to claim 1, wherein the method further comprises using the ECAP function to determine a cochlea response signal for the first recording electrode, which is above a second signal threshold level.

6. A method according to claim 1, wherein the first primary stimulation paradigm and the first secondary stimulation paradigm are the same.

7. A method according to claim 6, wherein the method further comprises using the ECAP function to select the second recording electrode and to determine a cochlea response signal for the second recording electrode, which is below a first signal threshold level.

8. A method according to claim 6, wherein the method further comprises using the ECAP function to determine a cochlea response signal for the first recording electrode, which is above a second signal threshold level.

9. A method according to claim 1, further comprising:
   applying stimulations corresponding to a second primary stimulation paradigm and a second secondary stimulation paradigm, respectively, to the stimulator electrode,
   recording a second primary cochlea response signal by the first recording electrode while applying the stimulation corresponding to the second primary stimulation paradigm,
   recording a second secondary cochlea response signal by the second recording electrode while applying the stimulation corresponding to the second secondary stimulation paradigm,
   using a difference between the first primary cochlea response signal and the second primary cochlea response signal to determine a main primary cochlea response signal,
   using a difference between the first secondary cochlea response signal and the second secondary cochlea response signal to determine a main secondary cochlea response signal, and
   using a difference between the main primary cochlea response signal and the main secondary cochlea response signal to determine the main electrically evoked compound action potential.

10. A method according to claim 9, wherein the stimulations respectively corresponding to the first primary stimulation paradigm and the first secondary stimulation paradigm include a single stimulation pulse, and the stimulations respectively corresponding to the second primary stimulation paradigm and the second secondary stimulation paradigm include multiple stimulation pulses.

11. A system for measuring a main electrically evoked compound action potential, the system comprising:
   a cochlea implant system which includes an electrode array, and where the electrode array includes at least a stimulator electrode, a first recording electrode and a second recording electrode, and where the first recording electrode is arranged closer to the stimulator electrode than the second recording electrode, a processor electrically in communication with the cochlea implant system, and the processor is configured to:

apply stimulations corresponding to a first primary stimulation paradigm and a first secondary stimulation paradigm, respectively, to the stimulator electrode, wherein the first recording electrode records a first primary cochlea response signal during application of the stimulation corresponding to the first primary stimulation paradigm, and the second recording electrode records a first secondary cochlea response signal during application of the stimulation corresponding to the first secondary stimulation paradigm, receive the first primary cochlea response signal recorded by the first recording electrode, and receive the first secondary cochlea response signal recorded by the second recording electrode, and calculate a difference between the first primary cochlea response signal and the first secondary cochlea response signal, and using the calculated difference to determine the main electrically evoked compound action potential, wherein the processor is configured to apply an ECAP function to select the first recording electrode and/or the second recording electrode, and wherein the processor is configured to use a pre-recorded cochlea response signal for each of the plurality of electrodes of the electrode array to determine the ECAP function.

12. A system according to claim 11, wherein the processor is further configured to:

apply other stimulations corresponding to a second primary stimulation paradigm and a second secondary stimulation paradigm, respectively, to the stimulator electrode, wherein the first recording electrode records a second primary cochlea response signal during application of the stimulation corresponding to the second primary stimulation paradigm, and the second recording electrode records a second secondary cochlea response signal during application of the stimulation corresponding to the second secondary stimulation paradigm, receive the second primary cochlea response signal recorded by the first recording electrode, and receive the second secondary cochlea response signal recorded by the second recording electrode, use the first primary cochlea response signal and the second primary cochlea response signal to determine a main primary cochlea response signal, use the first secondary cochlea response signal and the second secondary cochlea response signal to determine a main secondary cochlea response signal, and use a difference between the main primary cochlea response signal and the main secondary cochlea response signal to determine the main electrically evoked compound action potential.

13. A system according to claim 12, wherein the stimulations respectively corresponding to the first primary stimulation paradigm and the first secondary stimulation paradigm include a single stimulation pulse, and the stimulations respectively corresponding to the second primary stimulation paradigm and the second secondary stimulation paradigm include multiple stimulation pulses.

* * * * *